US00PP14459P39

(12) United States Plant Patent
Danziger

(10) Patent No.: US PP14,459 P3
(45) Date of Patent: Jan. 13, 2004

(54) SUTERA PLANT NAMED 'DANCOPLAV'

(50) Latin Name: *Sutera bacopa*
Varietal Denomination: Dancoplav

(75) Inventor: Gabriel Danziger, Nir-Zvi (IL)

(73) Assignee: Danziger Dan Flower Farm, Beit Dagan (IL)

( * ) Notice: Subject to any disclaimer, the term of this patent is extended or adjusted under 35 U.S.C. 154(b) by 0 days.

(21) Appl. No.: 10/105,243

(22) Filed: Mar. 26, 2002

(65) Prior Publication Data

US 2003/0188362 P1 Oct. 2, 2003

(51) Int. Cl.[7] ..... A01H 5/00

(52) U.S. Cl. ..... Plt./263

(58) Field of Search ..... Plt./263

*Primary Examiner*—Bruce R. Campell
*Assistant Examiner*—Michelle Kizilkaya
(74) *Attorney, Agent, or Firm*—Foley and Lardner

(57) ABSTRACT

A new and distinct Sutera plant named 'Dancoplav' characterized by having violet-blue flowers with yellow-orange throat; trailing, vigorous growth; early flowering; use as hanging baskets, combination planters and ground cover under full sunlight-slight shade.

2 Drawing Sheets

Latin name of the genus and species of the plant claimed: *Sutera bacopa.*

Variety denomination: 'Dancoplav'.

The present invention relates to a new and distinct cultivar of Sutera plant, botanically known as Bacopa, hereinafter referred to by the cultivar name 'Dancoplav'.

The new cultivar originated from a cross made in a controlled breeding program in Moshav Mishmar Hasiva, Israel. The female parent is an unpatented *Sutera bacopa* cultivar designated 'CV-01'. The male parent is an unpatented *Sutera bacopa* cultivar designated 'CV-012'. 'Dancoplav' was discovered and selected by the inventor, Gabriel Danziger, as a flowering plant within the progeny of the stated cross in a controlled environment in Moshav Mishmar Hasiva, Israel.

'Dancoplav' was selected in a cultivated environment in Moshav Mishmar Hasiva, Israel. Asexual reproduction of the new cultivar by Vegetative Cutting was first performed in December 2000 in Moshav Mishmar Hasiva, Israel and has demonstrated that the combination of characteristics as herein disclosed for the new cultivar are firmly fixed and retained through successive generations of asexual reproduction.

BRIEF SUMMARY OF THE INVENTION

The following traits have been repeatedly observed and are determined to be basic characteristics of 'Dancoplav' which in combination distinguish this Sutera as a new and distict cultivar:

1. Violet-blue flowers with yellow-orange throat;
2. Trailing vigorous growth;
3. Early flowering;
4. Use as hanging baskets, combination planters and ground cover under full sunlight-slight shade.

'Dancoplav' has not been observed under all possible environmental conditions. The phenotype of the new cultivar may vary significantly with variations in environment such as temperature, light intensity, and day length without any change in the genotype of the plant. The following observations, measurements and values descibe the new cultivar as grown in Moshav Mishmar Hasiva, Israel under conditions which closely approximate those generally used in commercial practice.

Of the many commercial cultivars known to the present inventor, the most similar in comparison to 'Dancoplav' is the cultivar 'Bacoble' (U.S. Plant Pat. No. 13,181), and the cultivar 'Yasflos' (U.S. Plant Pat. No. 12,616).

| | 'Dancoplav' | 'Bacoble' | 'Yasflos' |
|---|---|---|---|
| Flower color | Violet-Blue 91B | Violet 86C | Violet-Blue 94C |

BRIEF DESCRIPTION OF THE DRAWING

The accompanying photographic drawings illustrate the overall appearance of the new Sutera showing the colors as true as is reasonably possible with colored reproductions of this type. The plants are 2 months old, grown at a temperature range of 18–30 C, in natural daylight.

The first drawing shows 'Dancoplav' in its entirety.

The second drawing is a close-up of the flowers and leaves of 'Dancoplav'.

DETAILED BOTANICAL DESCRIPTION

The following observations, measurements and values describe the new cultivar as grown in Moshav Mishmar Hasiva, Israel under conditions which closely approximate those generally used in commercial practice. The new cultivar was grown as a pot plant in a 6 inch container, in a greenhouse during the winter.

Color refrences are made to The Royal Horticultural Society Colour Chart (R.H.S.), except where general colors of ordinary significance are used. Color values were taken under daylight conditions at approximately 12:00 pm. in Moshav Mishmar Hasiva, Israel. The age of the plant described is 2 months.

Parentage:

*Male parent.*—*Sutera bacopa* 'CV-01' from our breeding program.

*Female parent.*—*Sutera bacopa* 'CV-012' from our breeding program.

Classification:

*Botanical.*—*Sutera bacopa.*

*Commercial.*—*Sutera cv. Copia® Lavender.*

Propagation: Stem cutting.

Plant:

*General appearance and form.*—Height: 5 cm. Spread: 35 cm. across.

*Shape.*—Hemispherical to spherical, trailing Winter hardiness: Hardy in moderate climate. Vigor: Strong. Branching habit: Vigorously branched. Lateral branches:

| | Primary | Secondary |
|---|---|---|
| Length | 34 cm. | 11 cm. |
| Diameter | 2 mm. | 1 mm. |
| Intemode Length | 2.5 cm. | 3 cm. |
| Texture | Warty | Warty |
| Pubescence | Yes | Yes |
| Color | Green 137B | Green 137B |

*Rooting habit and description.*—Easy to root. Time to initiate roots: 7–10 days. Time to produce a rooted cutting: 14 days. Crop time: 4 weeks for loom flowering pot. Fragrance: Yes.

Foliage:

*Overall shape of leaf.*—Base Shape: Uneven.

*Apex shape.*—Acuminate. Margin: Crenulate. Form: Slightly convex. Texture: Smooth. Pubescence: Yes — slightly. Leaf length: 2.5 cm. Leaf width: 3 cm.

*Color of upper surface.*—Mature leaf: Yellow-Green 146A. Immature leaf: Yellow-Green 146B.

*Color of lower surface.*—Mature leaf: Yellow-Green 147B. Immature leaf: Yellow-Green 146B.

*Venation color.*—Upper surface: Yellow-Green 146A. Lower surface: Yellow-Green 146B.

*Petiole.*—Length: 10 mm. Diameter: 1 mm. Color: Yellow-Green 146B.

Flower description:

*Flowering response.*—Day naturally.

*Natural flowering season.*—All year round in moderate climate.

*Lastingness of the bloom.*—Flowering of a single flower lasts for 7 days.

*Quantity of flowers and buds per plant.*—Approx. 225.

*Flower size.*—Diameter at lobs: 13 mm. Diameter of corolla tube: 3 mm. Overall flower height: 10 mm.

*Flower bud.*—Height: 8 mm. Diameter: 3 mm. Color: Violet-Blue 91B. Shape: Spatulate.

*Petals.*—5. Shape: Obovate. Length: 5 mm. Width: 5 mm (as measured at petal center). Apex: Truncate. Margin: Entire. Texture: Slightly convex. Color: Upper surface, when opening: Violet-Blue 94D. Upper surface, opened flower: Violet-Blue 91B. Lower surface, when opening: Violet-Blue 91C. Lower surface, opened flower: Violet-Blue 91C.

*Corolla throat color.*—Yellow-Orange 17A.

*Calyx.*—Apearance: Deeply 5 lobed. Sepals: Shape: Linear. Texture: Smooth. Pubescence: Moderately present. Length: 6 mm. Diameter: 1 mm. Quantity: 5. Apex: Acute. Margin: Entire. Upper surface color: Yellow-Green 147B. Lower surface color: Yellow-Green 147B.

*Pedicel.*—Aspect: Slanted upward. Length: 7 mm. Diameter: 0.5 mm. Angle: 45°. Color: Yello-Green 146B.

Reproductive organs:

*Stamen.*—Number: 4. Color: Yellow-Orange 14A.

*Anthers.*—Color: Yellow-Orange 14A. Shape and length: Cylinder 1 mm.

*Pollen.*—Color: Yellow-Orange 14A. Quantity: Abundant.

*Pistils.*—Quantity: 1. Length: 10 mm.

*Stigma.*—Undulate. Color: Yellow-Green 146C.

*Style.*—Length: 8–10 mm. Color: Yellow-green 144C.

*Ovary.*—Color: Yellow-Green 146C.

*Seeds.*—Yes. Width: 9 fraction of mm. Length: 9 fraction of mm. Shape: Elliptic. Color: Gray-Orange 167A.

*Fruit.*—Yes. Color: Gray-Brown 199A.

Disease resistance: Unknown.

*General information.*—Light intensities: Full sunlight — Slight shade. Temperature: During day 20° C.–24° C., During night 16° C.–20° C. Tolerance: Tolerant to low and high temperatures. Fertilization: A balanced fertilizer with level of 100 ppm Nitrogen. Growth regulators: Not necessary.

I claim:

1. A new and distinct Sutera plant named 'Dancoplav', substantially as illustrated and described herein.

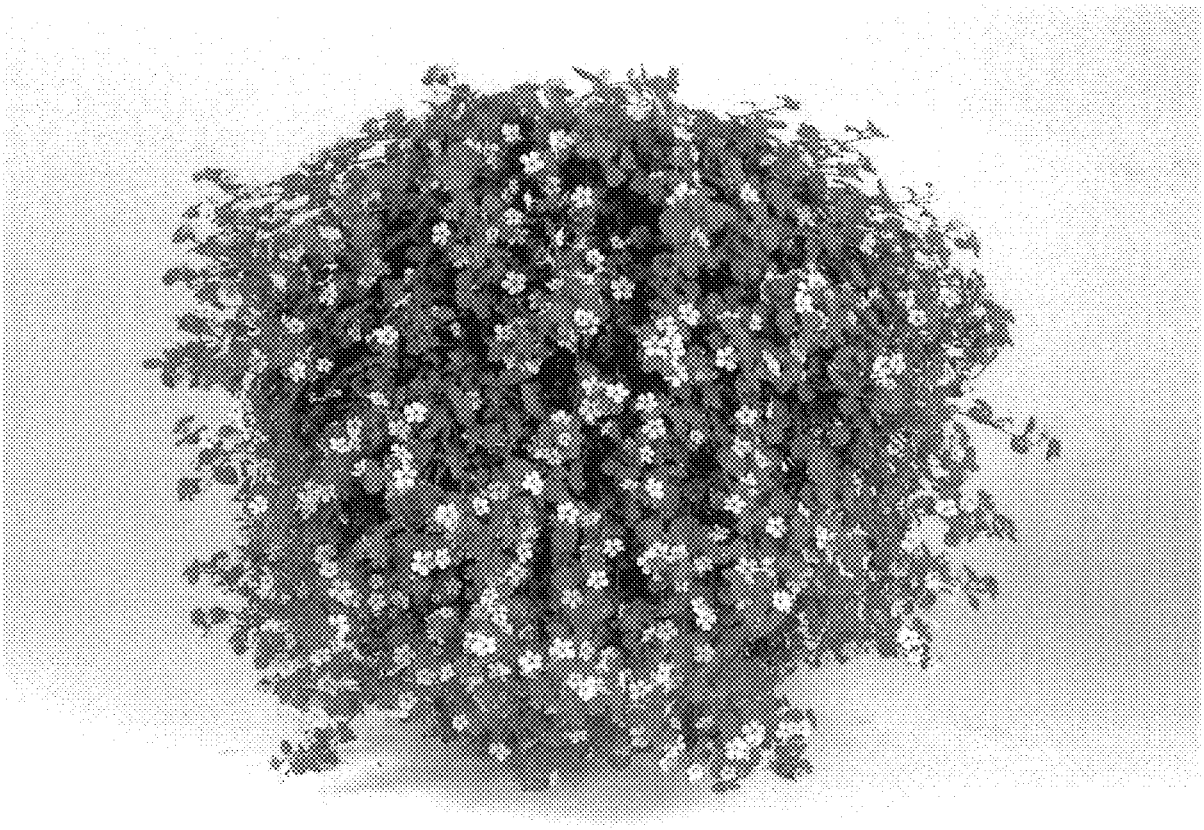

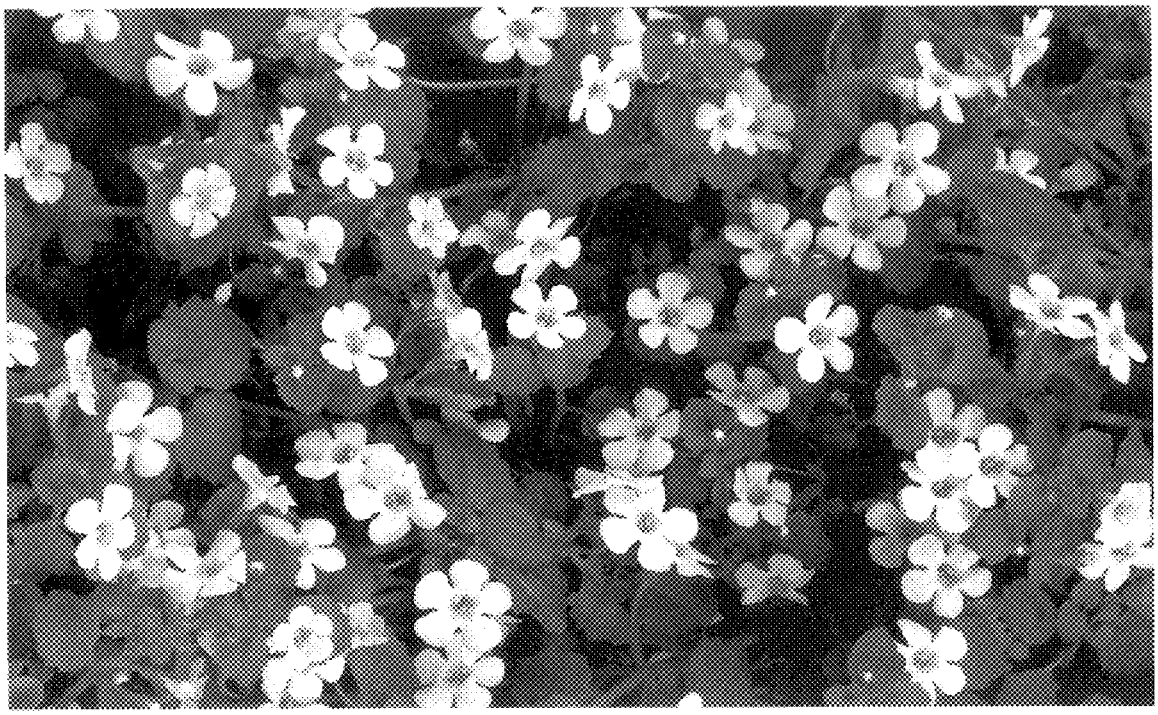

* * * * *